(12) United States Patent
Kutsch

(10) Patent No.: US 9,987,465 B2
(45) Date of Patent: Jun. 5, 2018

(54) WINDOW DRESSING HAVING FORCE CONCENTRATING ADHESION ELEMENTS

(75) Inventor: John Henry Kutsch, Harvard, IL (US)

(73) Assignee: Medline Industries, Inc., Northfield, IL (US)

( * ) Notice: Subject to any disclaimer, the term of this patent is extended or adjusted under 35 U.S.C. 154(b) by 1668 days.

(21) Appl. No.: 13/475,174

(22) Filed: May 18, 2012

(65) Prior Publication Data
US 2013/0310754 A1  Nov. 21, 2013

(51) Int. Cl.
*A61M 25/02* (2006.01)

(52) U.S. Cl.
CPC ..... *A61M 25/02* (2013.01); *A61M 2025/0266* (2013.01)

(58) Field of Classification Search
CPC ............ A61F 13/00076; A61F 13/0008; A61F 13/0246; A61F 13/025; A61F 13/0253; A61F 13/0256; A61F 13/0259; A61F 13/0263; A61F 13/0266; A61F 2013/00182; A61M 25/02; A61M 2025/0266; A61M 2025/0273
See application file for complete search history.

(56) References Cited

U.S. PATENT DOCUMENTS

| | | | |
|---|---|---|---|
| 4,485,809 A | 12/1984 | Dellas | |
| 4,600,001 A | 7/1986 | Gilman | |
| 4,641,643 A | 2/1987 | Greer | |
| RE33,727 E | 10/1991 | Sims | |
| 5,088,483 A | 2/1992 | Heinecke | |
| 5,160,315 A | 11/1992 | Heinecke | |
| 5,380,294 A | 1/1995 | Persson | |
| 5,520,629 A | 5/1996 | Heinecke et al. | |
| 5,531,855 A | 7/1996 | Heinecke | |
| 5,599,289 A | 2/1997 | Castellana | |

(Continued)

FOREIGN PATENT DOCUMENTS

| CA | 2400228 | 11/2008 |
|---|---|---|
| EP | 0353972 | 1/1994 |

(Continued)

OTHER PUBLICATIONS

Han, In Ho "International Search Report", PCT Serial No. PCT/US2013/039957; Filed May 7, 2013; dated Sep. 23, 2013.

(Continued)

*Primary Examiner* — Kami A Bosworth
(74) *Attorney, Agent, or Firm* — Philip H. Burrus, IV

(57) ABSTRACT

A dressing includes a cover layer and a plurality of force concentration elements disposed about a perimeter of the cover layer. Each force concentration element is configured to collect and distribute shearing forces applied to the dressing so as to retain the dressing to a patient. When configured as a window dressing, the window dressing can include a top layer defining a window and a backing layer coupled to the top layer and spanning the window. A plurality of adhesive islands can be disposed about a perimeter of the top layer, with each of the adhesive islands having a first adhesion coefficient associated therewith. An adhesive layer can be disposed about the adhesive islands. The adhesive layer can have a second adhesion coefficient associated therewith that is less than the first adhesion coefficient. Window dressings are well suited for catheterization procedures.

18 Claims, 12 Drawing Sheets

(56) References Cited

U.S. PATENT DOCUMENTS

| | | |
|---|---|---|
| 5,738,642 A | 4/1998 | Heinecke |
| 5,885,254 A | 3/1999 | Matyas |
| 5,968,000 A | 10/1999 | Harrison |
| 6,124,520 A | 9/2000 | Roberts |
| 6,124,521 A | 9/2000 | Roberts |
| 6,149,614 A | 11/2000 | Dunshee et al. |
| 6,169,224 B1 | 1/2001 | Heinecke |
| 6,187,126 B1 | 2/2001 | Rothrum |
| 6,242,665 B1 | 6/2001 | Malowaniec |
| 6,461,467 B2 | 10/2002 | Blatchford et al. |
| 6,685,682 B1 | 2/2004 | Heinecke |
| 6,706,940 B2 | 3/2004 | Worthley |
| 6,797,855 B2 | 9/2004 | Worthley |
| 6,841,715 B2 | 1/2005 | Roberts |
| 6,884,920 B2 | 4/2005 | Worthley |
| 6,998,511 B2 | 2/2006 | Worthley |
| 7,025,749 B2 | 4/2006 | Propp |
| 7,090,660 B2 | 8/2006 | Roberts et al. |
| 7,119,247 B2 | 10/2006 | Worthley |
| 7,294,751 B2 | 11/2007 | Propp et al. |
| 7,294,752 B1 | 11/2007 | Propp |
| D572,824 S | 7/2008 | Propp |
| 7,626,070 B2 | 12/2009 | Propp |
| 7,674,948 B2 | 3/2010 | Propp et al. |
| D634,423 S | 3/2011 | Heinecke |
| 8,049,057 B2 | 11/2011 | Propp |
| 8,049,058 B2 | 11/2011 | Propp |
| 8,053,623 B2 | 11/2011 | Propp |
| 8,053,624 B2 | 11/2011 | Propp |
| 8,212,101 B2 | 7/2012 | Propp |
| D679,402 S | 4/2013 | Heinecke |
| D679,403 S | 4/2013 | Heinecke |
| D690,425 S | 9/2013 | Heinecke |
| D695,901 S | 12/2013 | Heinecke |
| 2002/0169405 A1 | 11/2002 | Roberts |
| 2004/0077984 A1* | 4/2004 | Worthley ............... 602/55 |
| 2006/0211994 A1* | 9/2006 | Roman et al. ........... 604/180 |
| 2007/0049859 A1 | 3/2007 | Propp |
| 2008/0058692 A1 | 3/2008 | Propp et al. |
| 2008/0132821 A1 | 6/2008 | Propp et al. |
| 2010/0022933 A1 | 1/2010 | Oelund |
| 2010/0198161 A1 | 8/2010 | Propp |

FOREIGN PATENT DOCUMENTS

| | | |
|---|---|---|
| WO | WO-2013162680 | 4/2012 |
| WO | WO-2014003957 | 6/2012 |

OTHER PUBLICATIONS

"Market Watch Article", *Market Watch; 3M announces Next Generation of Tegaderm I.V. Advanced Securement Dressings*; Publication date Feb. 24, 2014.

"3M Brochure", *3M Brochure; 3M Tegaderm Family of Transparent Film Dressings: Application and Removal Techniques*; Published in 2008.

"3M Instruction Manual", *3M Tegaderm I.V. Advanced Securement Dressing with Comfort Adhesive Technology*; Publication 2010.

"3M Guide", *3M, 3M Tegaderm I.V. Advanced Securement Dressings Application and Removal Guide*; Publication date 2011.

* cited by examiner

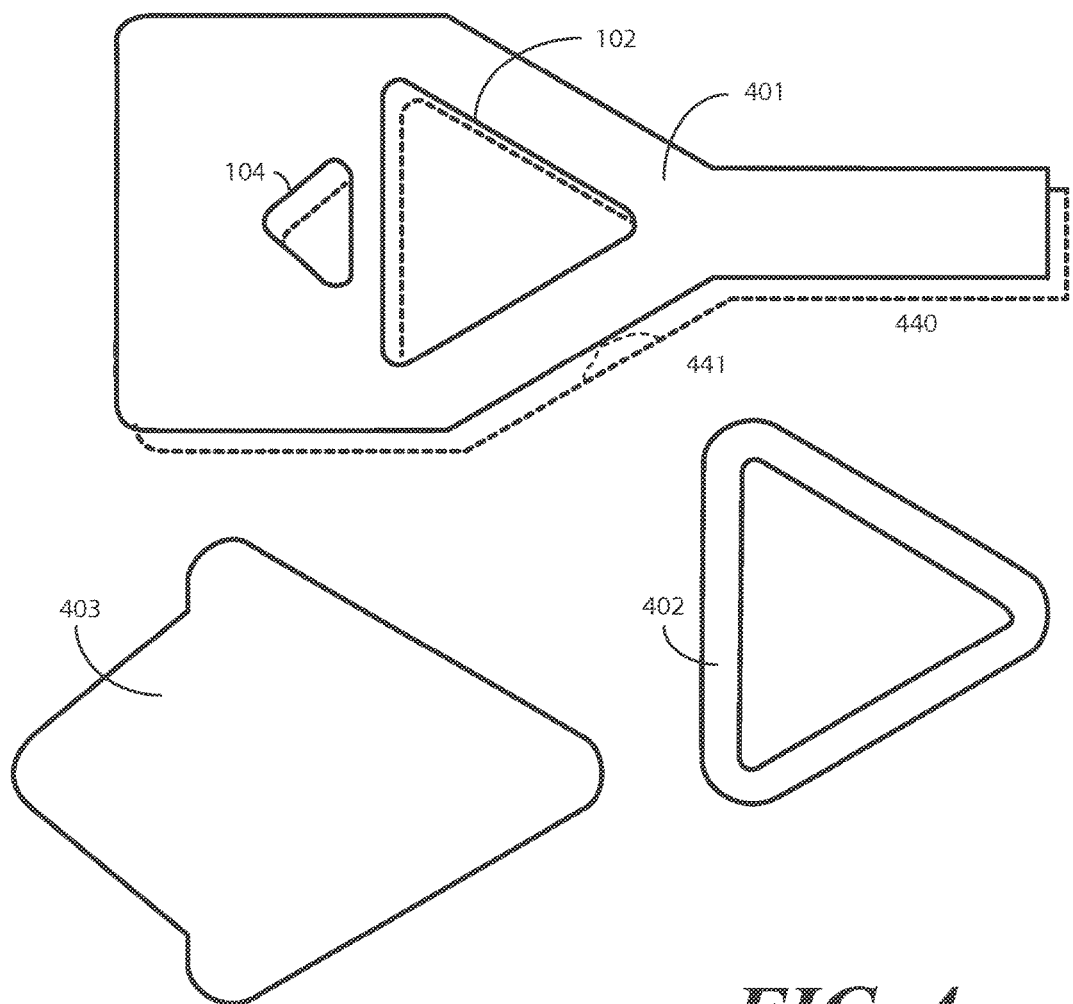
FIG. 4
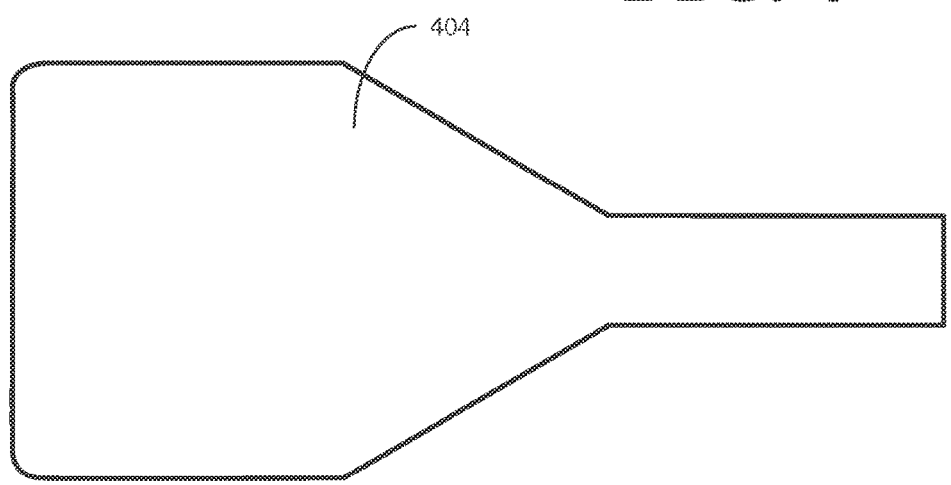

WINDOW DRESSING HAVING FORCE CONCENTRATING ADHESION ELEMENTS

BACKGROUND

Technical Field

This invention relates generally to dressings, and more particularly to a window dressing suitable for use in catheter and intravenous insertion procedures.

Background Art

Dressings are frequently used in wound treatment. Dressings are frequently applied to wounds to provide a protective covering, thereby helping the wound to heal. For example, many types of wounds are normally bandaged using a gauze and adhesive tape combination. The gauze can help to absorb any fluids emanating from the wound. The adhesive layer helps to retain the gauze in place atop the wound. One function of the dressing is to prevent infection of the wound. The dressing provides a barrier to materials that might contaminate the wound, including contaminating liquids or bacteria.

Dressings are also used in many medical procedures. In indwelling catheterization procedures for instance, such as when an intravenous catheter or peripherally inserted central catheter is inserted into a patient, adhesive strips with attached gauze can be used to provide closure for the wound or to secure the catheter to the patient. Such dressings employ gauze so as to adhere to the skin and catheter, but not to the insertion site.

One problem associated with prior art dressings is that the catheter and dressing can be easily removed. Consequently, it is quite easy to simply tug on the catheter to remove both the dressing and the catheter. There is thus a need for an improved dressing suitable for use with catheterization procedures.

BRIEF DESCRIPTION OF THE DRAWINGS

FIG. 4 illustrates constituent components of one explanatory dressing assembly configured in accordance with one or more embodiments of the invention.

Figure 1:
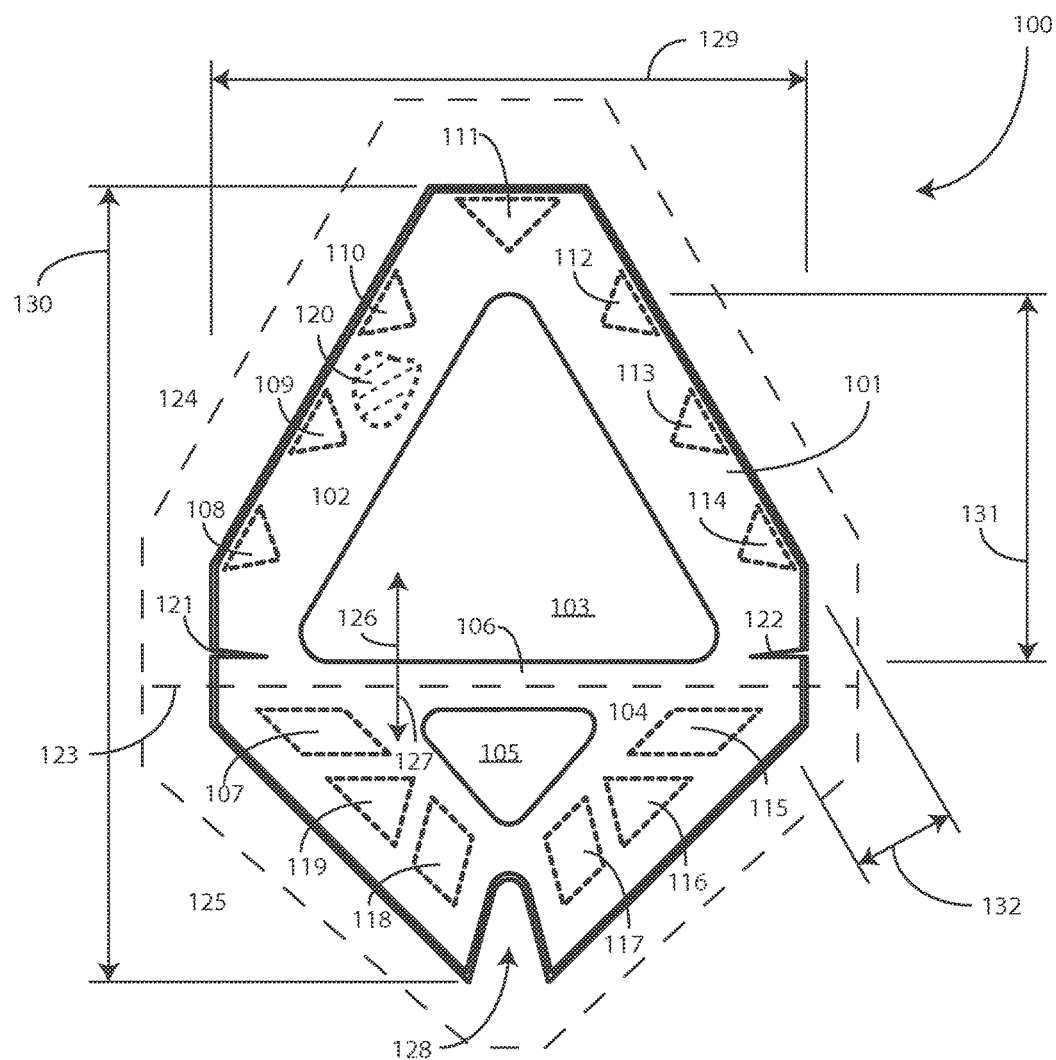
FIG. 1 illustrates one embodiment of a dressing configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

When a catheter has been inserted into a patient, the catheter needs to be secured to the patient to prevent the same from being dislodged from the insertion site. Dressings used to perform this function can take significant abuse, as they are frequently subjected to tugs, yanks, or other shearing forces that work to pull the catheter from the patient. Such shearing forces not only disturb the catheter, but disturb the patient as well. If the catheter is inadvertently removed from the insertion site, infection can occur. Further, the catheter must be reinserted, which can be an uncomfortable process for the patient.

Embodiments of the present invention provide a dressing suitable for use with intravenous catheter, peripherally inserted central catheter, and central venous catheter procedures. Embodiments of the dressing can be used to both protect the insertion site and to secure the catheter and prevent the same from dislodging in response to shearing, tugging, or other forces being applied to the catheter or the dressing. In some embodiments, the dressing can be packaged in sterile kits with additional medical implements used in the catheterization procedure. In other embodiments, the dressing can be packaged as a separate item in sterile packaging.

In one embodiment, a dressing includes a cover layer. The cover layer can be solid, or can define one or more windows where the dressing is intended to function as a window dressing. A plurality of force concentration elements is then disposed about a perimeter of the cover layer by selective printing of adhesives or other processes. Each force concentration element, in one embodiment, has an increased adhesion coefficient over adhesives surrounding the force concentration element. This disparate distribution of adhesion coefficients allows each force concentration element to collect and distribute shearing forces applied to the dressing—or a catheter disposed beneath the dressing—so as to retain the dressing and/or catheter to a patient.

In one embodiment, the force concentration elements are formed by selectively printing a plurality of adhesive "islands" about the perimeter of a top layer of the dressing. The term "island" is used herein to refer to a portion of the dressing having a characteristic different from surrounding portions of the dressing. Said differently, an adhesive "island" can be a portion of the dressing having a first adhesive coefficient that is completely surrounded by a second adhesive having a different adhesive coefficient. This will become clearer in the description of the figures that follows.

The adhesive islands can be configured by a selective printing process where the islands are printed only portions of the dressing, with surrounding portions being printed in a complementary fashion. Alternatively, the islands can be placed on the dressing by selective application from a web-fed rolling process where the islands are thermally or otherwise deposited from a carrier material during a pressing process. Such a process is described in U.S. Pat. No. 6,149,614 to Dunshee et al., which is incorporated herein by reference. The use of adhesive islands leverages a difference in the adhesive coefficients of the adhesive islands and the surrounding adhesive layer to safely bond the dressing to the skin and to distribute any tugging, yanking, or shearing forces across the various islands of securement.

In addition to the use of force concentration elements, some embodiments of the invention employ a unique shape to further help retain the dressing and/or catheter to the patient. In one or more embodiments, the cover layer has a first portion and second portion that adjoin at a medial line. The first portion extends along a first direction away from the medial line, while the second portion extends from the medial line distally in a second direction opposite the first. In one embodiment, the first portion is configured to be in a substantially trapezoidal shape. The second portion can also be substantially trapezoidal. However, in other embodiments intended for use with catheters, the second portion has an inverted-peak triangular shape. Using the force concentration elements, unique shape, and other elements described herein, embodiments of the present invention provide a robust solution configured to both protect the wound and retain the catheter to the patient.

In one or more embodiments, detachable, adhesive strips extend from the dressing. A medical practitioner can detach the strips and write notes, patient information, and so forth upon the strips. The strips can then be affixed to the patient, the patient's chart, or other objects. Where the strips are not needed, they can be discarded.

In one embodiment, the dressing is a window dressing in that a top layer defines a window across which a clear backing layer spans. The window allows a medical practitioner to see the insertion site without the need of removing the dressing from the skin. In another embodiment, the dressing is a dual-window dressing that includes two windows spanned by a backing layer. The first window can be used for viewing the insertion site, while the second window can be used to check for fluid accumulation about the catheter base. In one embodiment, a border can be placed about one or both windows. The border, which can be made from absorbent foam, gauze, or other material, serves as a wicking device to capture any fluids that may come from the catheter, the insertion site, or combinations thereof. Even where the border is included, the dressing is configured in a low profile, aesthetically pleasing design.

Embodiments of the present invention offer numerous advantages over prior art dressings and window dressings. The foremost advantage is adhesion, which is due in part to the use of adhesive islands and the unique shape of the dressing embodiments described herein. Prior art dressings attempt to retain catheters to the patient by using additional pieces of tape or stiffeners. Neither solution is effective. Requiring a medical practitioner to apply additional pieces of tape is time consuming and cumbersome. Further, the end result, i.e., a dressing being applied with numerous pieces of tape being applied atop the dressing, is unsightly and haphazard. Where the dressing is a window dressing, additional tape can make it impossible to see through the window. The inclusion of stiffeners can be uncomfortable to the patient and can even make it easier for the dressing or catheter to be removed by shearing forces. By contrast, the shape and design of both the dressing and the adhesive islands of embodiments of the present invention provide improved strength against shearing forces over prior art designs in addition to providing a singular, aesthetically pleasing appearance that does not require additional tape of adhesives. Embodiments of the present invention increase the overall surface area of adhesion and improve the placement and type of adhesion elements to improve fixturing of the various dressings. Additionally, the design of embodiments described below can be alternately rotated by 180 degrees on a panel so as to be manufactured with minimal waste. This decreases not only overall cost, but negative environmental impact as well.

Turning now to FIG. 1, illustrated therein is one embodiment of a dressing 100 configured in accordance with one or more embodiments of the invention. The dressing 100 of FIG. 1 is configured as a "window" dressing because it included two windows 102,104 that are covered by a pellucid backing layer 103,105 so that a medical practitioner can see through each window 102,104. It will be clear to those of ordinary skill in the art having the benefit of this disclosure that the dressing 100 could be solid without windows for other applications. The window dressing is merely one example of a dressing configuration that will be used for explanatory purposes.

The dressing 100 includes a top layer 101, which in this embodiment defines two windows 102,104. The top layer 101, which serves as a cover layer for the dressing, is manufactured in one embodiment from a spun polyester material. For example, in one explanatory embodiment, the top layer 101 is manufactured from 35-gram spun polyester. This material is well suited for the top layer 101 because it is breathable and provides a wicking capability for stray fluids.

Those of ordinary skill in the art having the benefit of this disclosure will appreciate that spun polyester is but one type of material suitable for the backing layer. Plastic-based materials, rubber-based materials, elastic fabrics, or other materials may also be used. Additionally, various woven, non-woven, hydroentangled materials, and/or combinations thereof, absorbent Airlaid, spunlace, blends of polyester, polypropylene, polyethylene, urethane, and/or combinations thereof can be used. These materials can be manufactured using various methods, including a spunbond metblown spundbond method, a spunbond metblown metblown spundbond method, and a spunbond metblown metblown spundbond method. It will be clear to those of ordinary skill in the art having the benefit of this invention that the top layer 101 can be manufactured from other materials as well. For example, in one embodiment the top layer 101 is manufactured from two layers that are coupled together. A first layer can comprise, for example, a blue thermo-polyehtylene (TPE) film that is covered in adhesive. Atop the TPE layer is disposed another layer, which may be manufactured from Sontara®, which is manufactured by the DuPont Corporation.

As noted above, the top layer 101 of this illustrative embodiment defines two windows 102,104. The windows 102,104 of this explanatory embodiment are substantially triangular in shape, with the bases of each triangle abutting an isthmus 106 of the top layer 101. In this illustrative embodiment, the isthmus 106 is located at a medial line 123 of the top layer 101 that separates a first portion 124 of the dressing 100 from a second portion 125 of the dressing 100. It will be clear to those of ordinary skill in the art having the benefit of this disclosure that the windows 102,104 can take other shapes as well, including circular, ovular, rectangular, multi-sided polygonal, and so forth. The illustrative isthmus 106 of FIG. 1 is about 0.30 inches wide. The term "about" is used to refer to dimensions inclusive of manufacturing tolerances. Thus, "about 0.30 inches wide" can comprise 0.286 inches or 0.302 inches where the manufacturing tolerances are plus or minus 0.015 inches.

Each window 102,104 of this illustrative embodiment is covered by a backing layer 103,105. Said differently, a backing layer 103,105 is coupled to the top layer 101 such that it spans and covers or "closes" each window 102,104 of the dressing 100. The backing layers 103,105 can be integrated into a single backing layer or can be separated from each other. In one embodiment, the backing layers 103,105 are pellucid to allow a medical practitioner to see through each window 102,104.

In one embodiment the backing layers 103,105 are manufactured from a thermoplastic polyethylene film (TPE). Alternatively, a thermoplastic polyurethane (TPU) can be used. The TPU or TPE can be configured to be breathable via the inclusion of micropores that allow vapor to penetrate the TPU or TPE while precluding liquids from passing through the same. While other materials—be they breathable or not—can be used, vapor penetrable backing material can help wounds heal more quickly. Breathable TPU and TPE materials are available from companies such as American Polyfilm, Inc., of Brandford, Conn. Breathable TPU or TPE is well suited as the backing layer 103,105 due to its high durability, high abrasion resistance, and low-temperature flexibility. In one embodiment, the backing layers 103,105 are manufactured from textured, breathable TPU or TPE having an adhesive layer disposed along a patient side of the backing layer 103,105.

Disposed about the windows 102,104 of the explanatory embodiment of FIG. 1, and thus about a perimeter of the top layer 101 of the dressing 100, are a plurality of adhesive islands 107,108,109,110,111,112,113,114,115,116,117,118, 119. At least twelve adhesive islands 107,108,109,110,111, 112,113,114,115,116,117,118,119 are shown in the embodiment of FIG. 1. An adhesive layer 120 is disposed about each of the adhesive islands 107,108,109,110,111,112,113, 114,115,116,117,118,119 such that at least a portion of the adhesive layer 120 entirely surrounds each adhesive island 107,108,109,110,111,112,113,114,115,116,117,118,119. Said differently, an adhesive layer 120 is then disposed along the bottom of the top layer 101 along portions outside of the adhesive islands 107,108,109,110,111,112,113,114,115,116, 117,118,119 such that the adhesive layer 120 surrounds each of the adhesive islands 107,108,109,110,111,112,113,114, 115,116,117,118,119.

Note that the view shown in FIG. 1 is a top plan view. The top of the dressing 100 is sometimes referred to as the "medical practitioner" side, as it is the side that faces away from the patient and towards the medical practitioner. The bottom of the dressing 100 is sometimes referred to as the "patient side" as it is the side that contacts the patient. The adhesive layer 120 and the adhesive islands 107,108,109, 110,111,112,113,114,115,116,117,118,119 of this illustrative embodiment are each disposed on the bottom side of the top layer 101. Accordingly, they are shown with dashed lines.

In one embodiment, the adhesive islands 107,108,109, 110,111,112,113,114,115,116,117,118,119 and adhesive layer 120 can be deposited on the bottom of the top layer 101 by a selective printing process. In such a process, either the adhesive islands 107,108,109,110,111,112,113,114,115,116, 117,118,119 or the adhesive layer 120 can be deposited first by printing adhesive, with the other being printed second in a complementary fashion. For example, in one embodiment, the adhesive islands 107,108,109,110,111,112,113,114,115, 116,117,118,119 can be deposited first. In the next step, the adhesive layer 120 can be deposited across the bottom of the top layer 101 in all locations not occupied by the adhesive islands 107,108,109,110,111,112,113,114,115,116,117,118, 119. Conversely, the adhesive layer 120 can be selectively deposited by leaving selective voids where the adhesive islands 107,108,109,110,111,112,113,114,115,116,117,118, 119 will eventually be placed. The adhesive islands 107, 108,109,110,111,112,113,114,115,116,117,118,119 can then be deposited in the voids. In yet another process, the adhesive layer 120 can be placed across the entirety of the bottom of the top layer 101. After this step, the adhesive islands 107,108,109,110,111,112,113,114,115,116,117,118, 119 can be selectively placed atop portions of the adhesive layer 120 such that the adhesive layer surrounds each of the adhesive islands 107,108,109,110,111,112,113,114,115,116, 117,118,119.

In one embodiment, the adhesive deposited on the top layer 101 to form the adhesive islands 107,108,109,110,111, 112,113,114,115,116,117,118,119 is a medical grade adhesive manufactured by companies such as Hollister or 3M. One example includes Scotch-Weld™ adhesive manufactured by 3M Corporation. Another is cynoacrolate, which is manufactured by a variety of manufacturers. The adhesive used for the adhesive layer 120 can be the same adhesive, or can be a different adhesive.

Each of the adhesive islands 107,108,109,110,111,112, 113,114,115,116,117,118,119 of this embodiment has an adhesion coefficient associated therewith. The adhesion coefficient, sometimes referred to as the "tack," is a measurement of the stickiness of the material disposed along the top layer 101 within each of the adhesive islands 107,108, 109,110,111,112,113,114,115,116,117,118,119. One way of measuring the adhesion coefficient is by determining what amount of weight can be supported by a square centimeter of the adhesive material disposed within each of the adhesive islands 107,108,109,110,111,112,113,114,115,116,117, 118,119. Where a square inch of the material is capable of supporting a greater weight, it will have a greater adhesion coefficient, and vice versa.

Similarly, the adhesion layer 120 has an adhesion coefficient as well. In one embodiment, the adhesive coefficient of the adhesive islands 107,108,109,110,111,112,113,114, 115,116,117,118,119 and the adhesive coefficient of the adhesive layer 120 are different. Specifically, in one embodiment, the adhesion coefficient of the adhesive islands 107, 108,109,110,111,112,113,114,115,116,117,118,119 is greater than the adhesive coefficient of the adhesive layer 120. In such an embodiment embodiment, the second adhesion coefficient, which is associated with the adhesive layer 120, is less than the first adhesion coefficient, which is associated with the adhesive islands 107,108,109,110,111,112,113,114, 115,116,117,118,119.

Where the adhesive used for the adhesive layer 120 is the same type or brand as that used for the adhesive islands 107,108,109,110,111,112,113,114,115,116,117,118,119, the adhesive layer and adhesive islands 107,108,109,110,111, 112,113,114,115,116,117,118,119 can still have different adhesion coefficients. Many adhesives available on the market are available with different adhesion coefficients. Accordingly, in one embodiment, the same brand of adhesive can be selected with different adhesion coefficients such that the adhesive used for the adhesive islands 107,108,109, 110,111,112,113,114,115,116,117,118,119 is "stickier" than that used for the adhesive layer 120. Similarly, where different adhesives are used, the adhesion coefficient of the adhesive layer 120 can be less than that of the adhesive islands 107,108,109,110,111,112,113,114,115,116,117,118, 119.

The use of disparate adhesion coefficients allows the adhesive islands 107,108,109,110,111,112,113,114,115,116, 117,118,119 to function as force collection elements in that shearing forces are concentrated at the stickier portions of the adhesive islands 107,108,109,110,111,112,113,114,115, 116,117,118,119 rather than being generally across the top layer 101. This helps to retain the dressing 100 to the patient by providing anchors of increased resistance at strategic locations along the bottom of the top layer 101.

In one embodiment, the adhesive islands 107,108,109, 110,111,112,113,114,115,116,117,118,119 are configured so as to be visibly distinct from the adhesive layer 120. This can be achieved by coloring the adhesive used for the adhesive islands 107,108,109,110,111,112,113,114,115,116,117,118, 119 differently from that used for the adhesive layer 120. For example, the adhesive islands 107,108,109,110,111,112,113, 114,115,116,117,118,119 can be blue, while the adhesive layer 120 is green, and so forth. In other embodiments, such as where the adhesives used for the adhesive islands 107, 108,109,110,111,112,113,114,115,116,117,118,119 and the adhesive layer 120 are clear, visible demarcations such as perimeter outlines can be placed about the adhesive islands 107,108,109,110,111,112,113,114,115,116,117,118,119 for ease of visibility. In yet another embodiment, the height or texture of the adhesive islands 107,108,109,110,111,112, 113,114,115,116,117,118,119 can be different from that of the adhesive layer 120. Other examples if visible distinctions will be obvious to those of ordinary skill in the art having the benefit of this disclosure.

The adhesive islands 107,108,109,110,111,112,113,114, 115,116,117,118,119 can take different shapes. For example, adhesive island 107 is substantially rectangular. Adhesive island 108 is substantially triangular. In the illustrative embodiment of FIG. 1, at least some of the plurality of adhesive islands 107,108,109,110,111,112,113,114,115,116, 117,118,119, i.e., adhesive islands 108,109,110,111,112,113, 114,116, have substantially triangular perimeters. At least some other of the adhesive islands 107,108,109,110,111,112, 113,114,115,116,117,118,119, i.e., adhesive islands 107,115, 117,118, have substantially rectangular perimeters.

In one embodiment, optional stress relief elements 121, 122 are provided at a proximal location relative to the medial line 123 of the dressing 100. The stress relief elements 121,122 of this illustrative embodiment are also substantially aligned with a side of window 102 abutting the isthmus 106. The inclusion of stress relief elements 121,122 provides strain relief between the first portion 124 of the dressing 100 and the second portion 125 of the dressing. While two stress relief elements 121,122 are shown in FIG. 1, it will be clear to those of ordinary skill in the art having the benefit of this disclosure that additional stress relief elements can be added as well. For example, in one embodiment, four stress relief elements are included, with two being substantially aligned with the side of window 102 abutting the isthmus 106 and two others being substantially aligned with the side of window 104 abutting the isthmus 106. The use of more than two stress elements can be beneficial when the overall size of the dressing 100 becomes larger.

As noted above, in this illustrative embodiment, a medial line 123 separates a first portion 124 of the dressing 100 from a second portion 125 of the dressing. The first portion 124 extends along a first direction 126 away from the medial line 123, while the second portion 125 extends along an opposite direction 127 from the medial line. As also noted above, the overall shape of the dressing 100 can help in retaining the dressing 100 and/or a catheter to the patient. In this illustrative embodiment, the first portion 124 is substantially trapezoidal in shape.

The second portion 125 can likewise be substantially trapezoidal in shape. However, in the illustrative embodiment of FIG. 1, the second portion 125 is inverted-peak triangular in shape. Looking at the plan view of FIG. 1, the second portion 125 appears to be an inverted triangle with its peak turned back on itself by curved, concave inlet 128. The use of this inverted-peak triangular shape is useful in catheter procedures as the tube connected to the catheter can extend outwardly from under the dressing 100 through the curved, concave inlet 128.

The dressing 100 can come in different sizes. For example, in one embodiment, the width 129 is about 2.48 inches. In such an embodiment, there may be no need to include stress relief elements. In another embodiment, the width 129 is about 3.81 inches. In this embodiment, two stress relief elements can be included. In yet another embodiment, the width 129 is about 4.99 inches. In this embodiment, four or more stress relief elements can be used. These stress relief elements can be located at corners of the dressing 100 occurring just above and below the medial line 123. In one embodiment well suited for catheterization procedures, the width 129 is about 3.72 inches.

Similarly, the height 130 can vary as well. In one embodiment the height 130 is about 3.22 inches. In another embodiment, the height 130 is about 5 inches. In yet another embodiment, the height is about 6.5 inches. In one embodiment well suited for catheterization procedures, the height 130 is about 4.98 inches.

Just as the height 130 and width 129 of the dressing 100 can be varied, so too can the size of the windows 102,104 (where included). For example, in one embodiment well suited for catheterization procedures, window 102 is configured as an isosceles triangle with rounded corners having a height 131 of about 2.3 inches. In a smaller embodiment, the height 131 of window 102 is about 1.48 inches. In a larger embodiment, the height 131 of window 102 is about 3 inches. Window 104 can be varied with similar proportions.

As with the other dimensions, the thickness 132 of the perimeter portion of the top layer 101 can vary as well. For example, in one embodiment well suited for catheterization procedures, the thickness 132 of the perimeter portion is about 0.68 inches. In a smaller embodiment, the thickness 132 of the perimeter portion is about 0.44 inches. In a larger embodiment, the thickness 132 of the perimeter portion is about 0.88 inches.

When the bottom of the dressing 100 is covered with adhesive, a releasable layer of wax release backing paper (not shown) can be applied to the adhesive to keep it from sticking to itself or other objects in packaging. A user or medical practitioner would first remove the wax release backing paper when removing the dressing 100 from a package, thereby exposing the adhesive.

Figure 2:
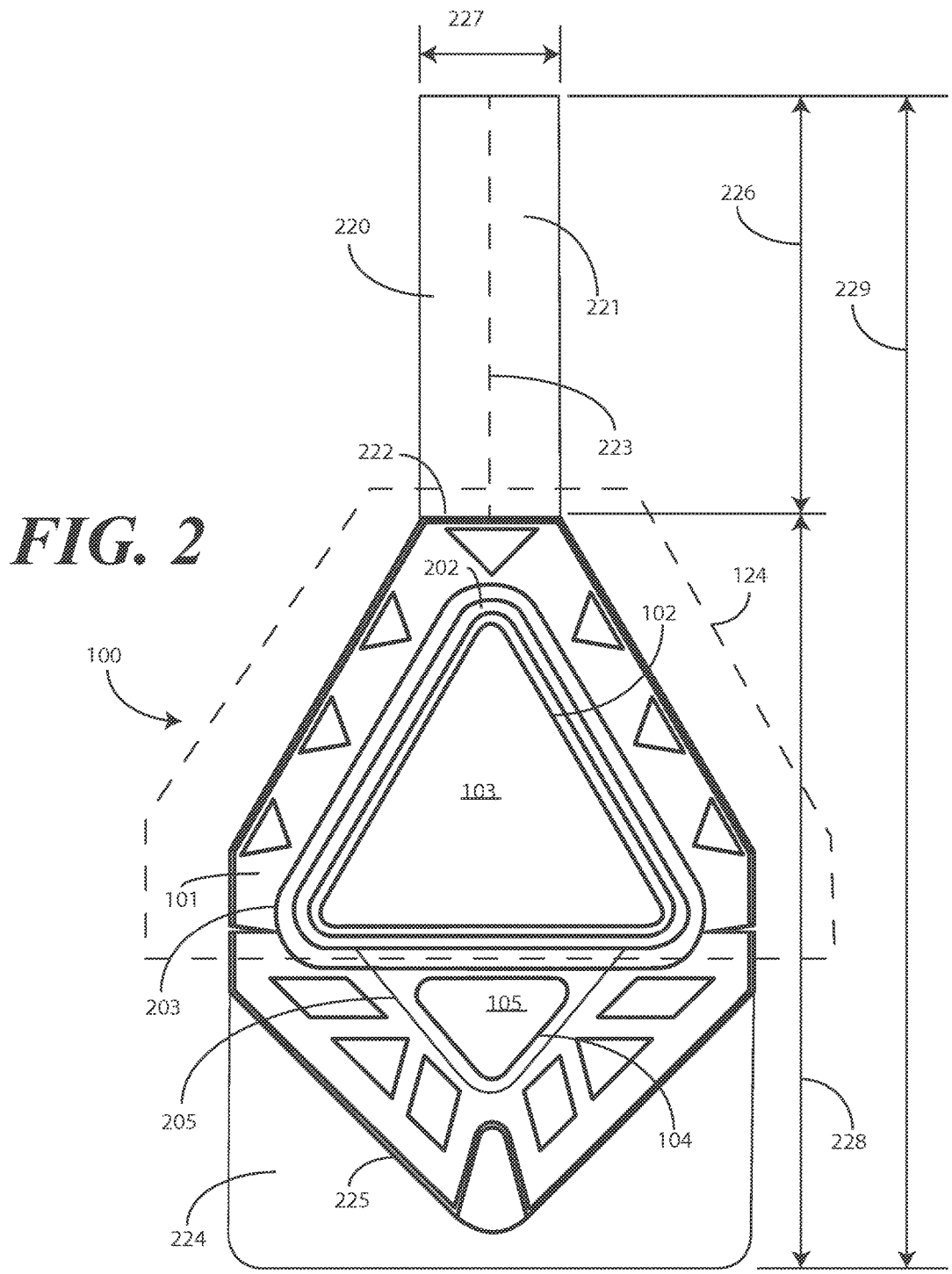
FIG. 2 illustrates another embodiment of a dressing assembly configured in accordance with one or more embodiments of the invention.
Figure 3:
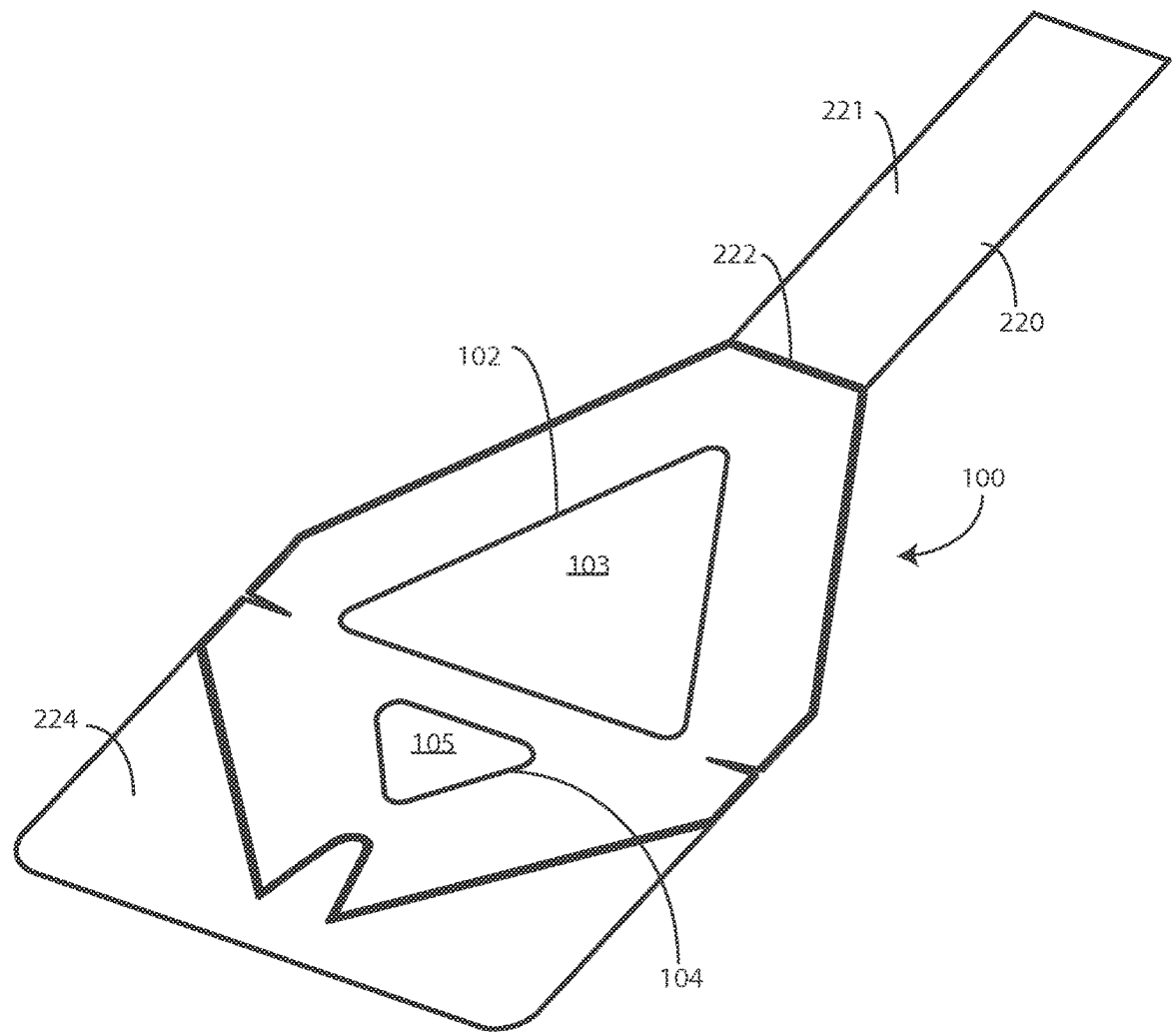
FIG. 3 illustrates a perspective view of another embodiment of a dressing assembly configured in accordance with one or more embodiments of the invention.

Turning now to FIGS. 2 and 3, illustrated therein is one embodiment of a dressing assembly 200 configured for easy manufacture. The dressing assembly 200 includes the dressing 100 of FIG. 1 along with additional, optional elements. Note that the view of FIG. 2 is a bottom plan view of the dressing assembly 200, while FIG. 3 is a top perspective view.

Prior to discussing the dressing assembly 200, there are a few elements of the dressing 100 of FIG. 1 that can be seen in the bottom plan view of FIG. 2 that were hidden in the top plan view of FIG. 1. For example, in the bottom plan view of FIG. 2, the perimeter 203 of the backing layer 103 spanning window 102 can be seen, as can the perimeter 205 of the backing layer 105 covering window 104. In this illustrative embodiment, backing layer 103 and backing layer 105 are formed by a single piece of clear, breathable, thermoplastic polyethylene or polyurethane film. The backing layers 103,105 are adhesively coupled to the top layer 101 in this illustrative embodiment. However, they could be thermally bonded together or coupled together by other methods.

Next, in this illustrative embodiment, an absorptive surround 202 has been disposed about window 102. The absorptive surround 202 is an absorptive material configured to wick any liquids being released from a wound, catheter insertion site, catheter, or combinations thereof. In one embodiment, the absorptive surround 202 comprises a cotton-felt material. In another embodiment, the absorptive surround comprises 5 oz. gauze. Combinations of absorptive materials could also be used. Anti-microbial, antibiotic, and anti-bacterial substances can be added to the absorptive surround as well.

The dressing assembly 200 of FIG. 2. Includes a pair of adhesively backed label strips 220,221 extending distally from the top of the first portion 124 of the dressing 100. In one embodiment, the adhesively backed label strips 220,221 can be selectively detachable from the dressing 100 by way of a score line 222 or perforation. Similarly, each adhesively backed label strip 220,221 can be selectively detached from the other by a score line or perforation 223. A medical practitioner can use the adhesively backed label strips 220, 221 to write notes, patient information, medication information, or other information thereon. The adhesively backed label strips 220,221 can then be attached to the patient, catheter, drip bag, patient chart, medical record, or other object. Where they are not needed, the adhesively backed label strips 220,221 can be discarded. In one illustrative embodiment, the adhesively backed label strips 220,221 have a height 226 of about 3 inches and a width 227 of about 0.98 inches.

At the opposite side of the dressing 100 is a tailpiece 224 that can be separable from the dressing 100 by way of a score line 225 or perforation. The tailpiece 224 is a manufacturing aid that can be used to pass the dressing assembly 200 through machinery in an automated assembly process. In one embodiment, the height 228 of the dressing 100 and the tailpiece 224 is about 5.35 inches, giving the overall dressing assembly 200 a height 229 of about 8.35 inches.

Turning to FIGS. 4-9, illustrated therein are graphical method steps for manufacturing a window dressing configured in accordance with one or more embodiments of the invention. Beginning with FIG. 4, illustrated therein are the basic components for one embodiment of the dressing. These elements include a dressing assembly cover layer 401, a backing layer 403, an absorptive surround 402, and a wax release backing paper 404. The cover layer 401 has been die cut in this embodiment to include two windows 102,104. Additionally, the cover layer 401 has been cut to reveal the starting portions of what will become the adhesively backed label strips (220,221). The wax release backing paper 404 has been cut in a complementary fashion.

In one optional embodiment, the cover layer 401 can be manufactured from multiple layers. For example, the cover layer 401 can be manufactured from a first material, such as Sontara® manufactured by DuPont. A second layer 440, which can be a TPE or TPU layer, can then be disposed beneath the cover layer 401. An adhesive 441 can be disposed atop the second layer 440, where used, to bind it to the cover layer 401. In one or more embodiments, the second layer 440 can be colored so as to provide an easily visible appearance. For example, in one embodiment, the second layer 440 is blue. Other colors may be chosen as well.

The backing layer 403, which in this embodiment is a pellucid layer of breathable thermoplastic polyethylene film, is configured as a unitary piece of film that will span both windows 102,104. The absorptive surround 402, configured here as 5-gram gauze, has been cut such that window 102 will fit within an aperture defined within the absorptive surround 402.

Figure 5:
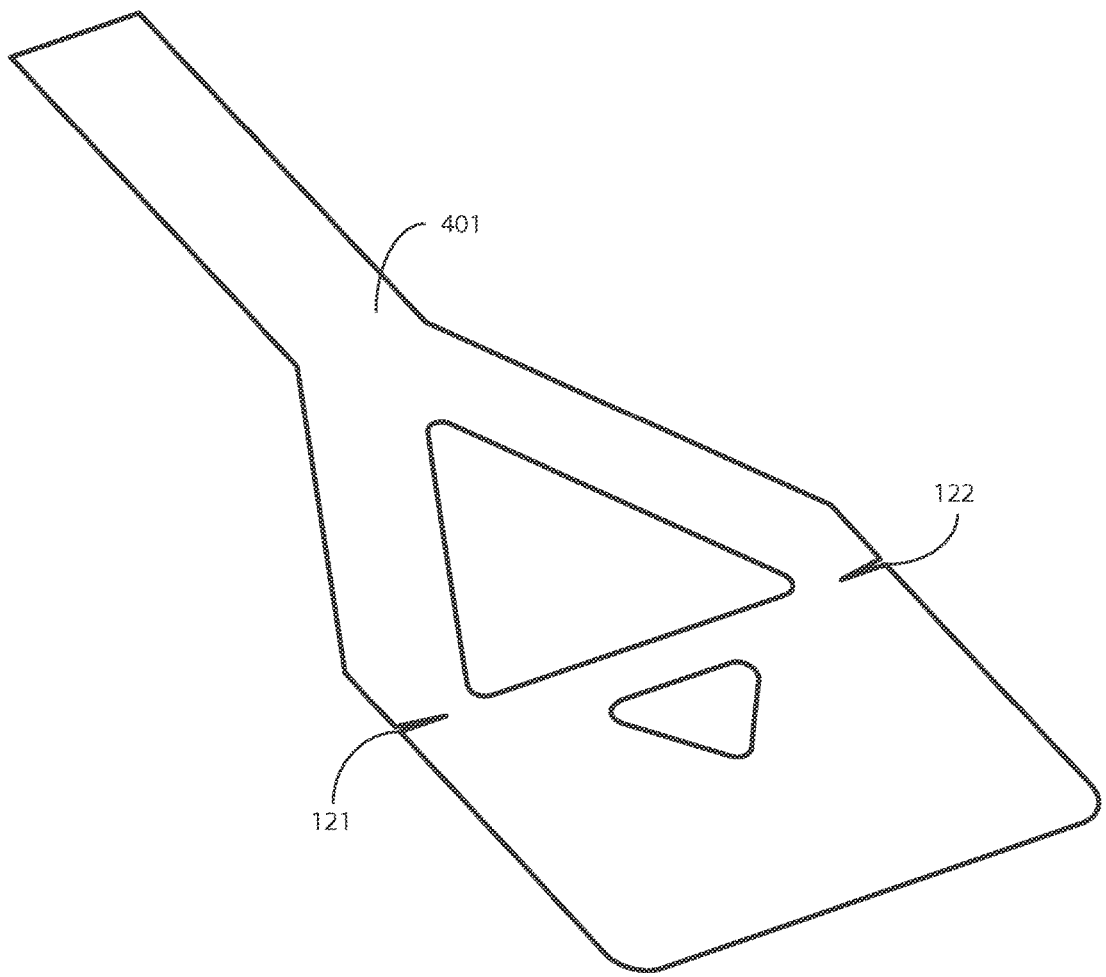
FIG. 5 illustrates a step in a method of manufacturing an explanatory dressing assembly configured in accordance with one or more embodiments of the invention.

Turning now to FIG. 5, illustrated therein is an optional manufacturing step. As shown, the cover layer 401 can optionally be cut so as to include the stress relief elements 121,122 described above. While two stress relief elements 121,122 are shown in FIG. 4, four, six, or more stress relief elements can be included in some embodiments.

Figure 6:
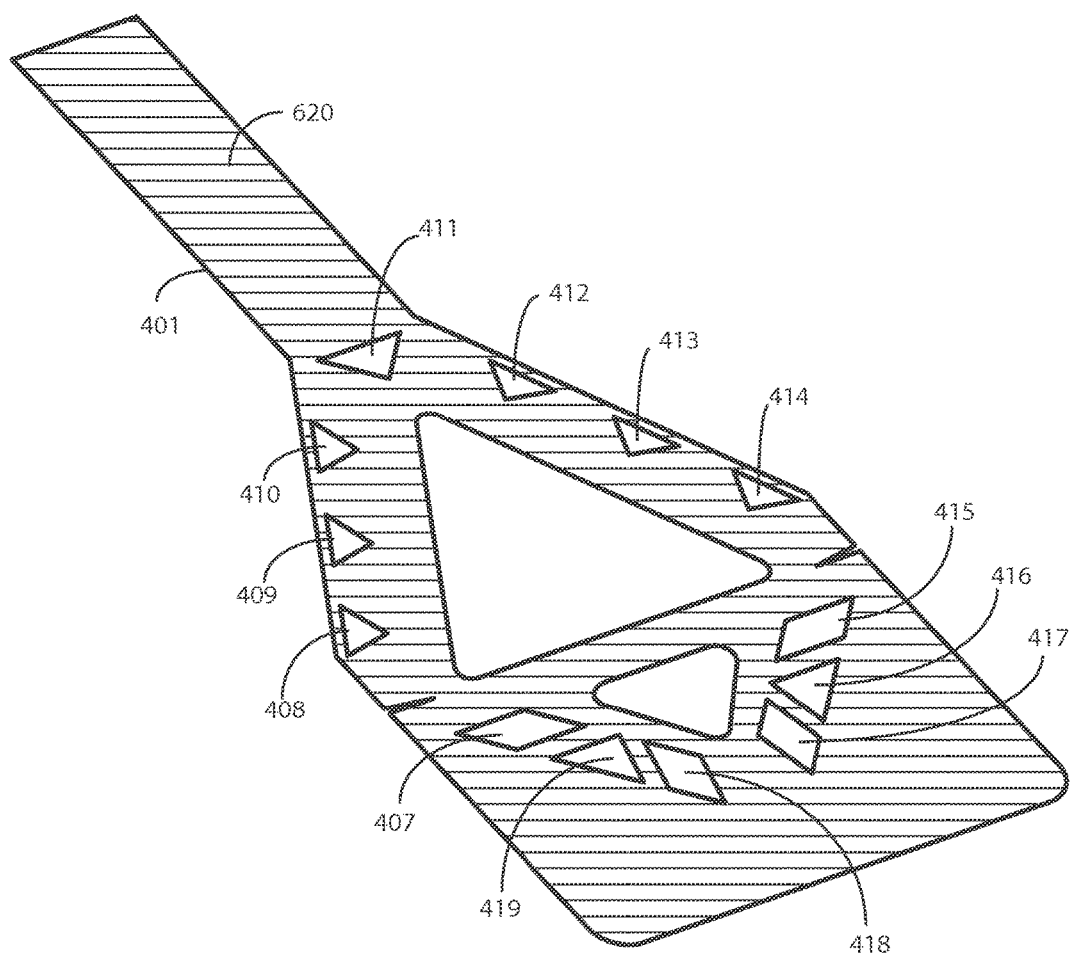
FIG. 6 illustrates another step in a method of manufacturing an explanatory dressing assembly configured in accordance with one or more embodiments of the invention.

Turning to FIG. 6, an adhesive layer 620 is applied to the bottom of the cover layer 401. As shown, the adhesive layer 620 is selectively deposited by way of a selective printing process. This leaves voids 407,408,409,410,411,412,413, 414,415,416,417,418,419 into which another adhesive, having a higher adhesion coefficient in one embodiment, can be deposited to form adhesive islands.

Figure 7:
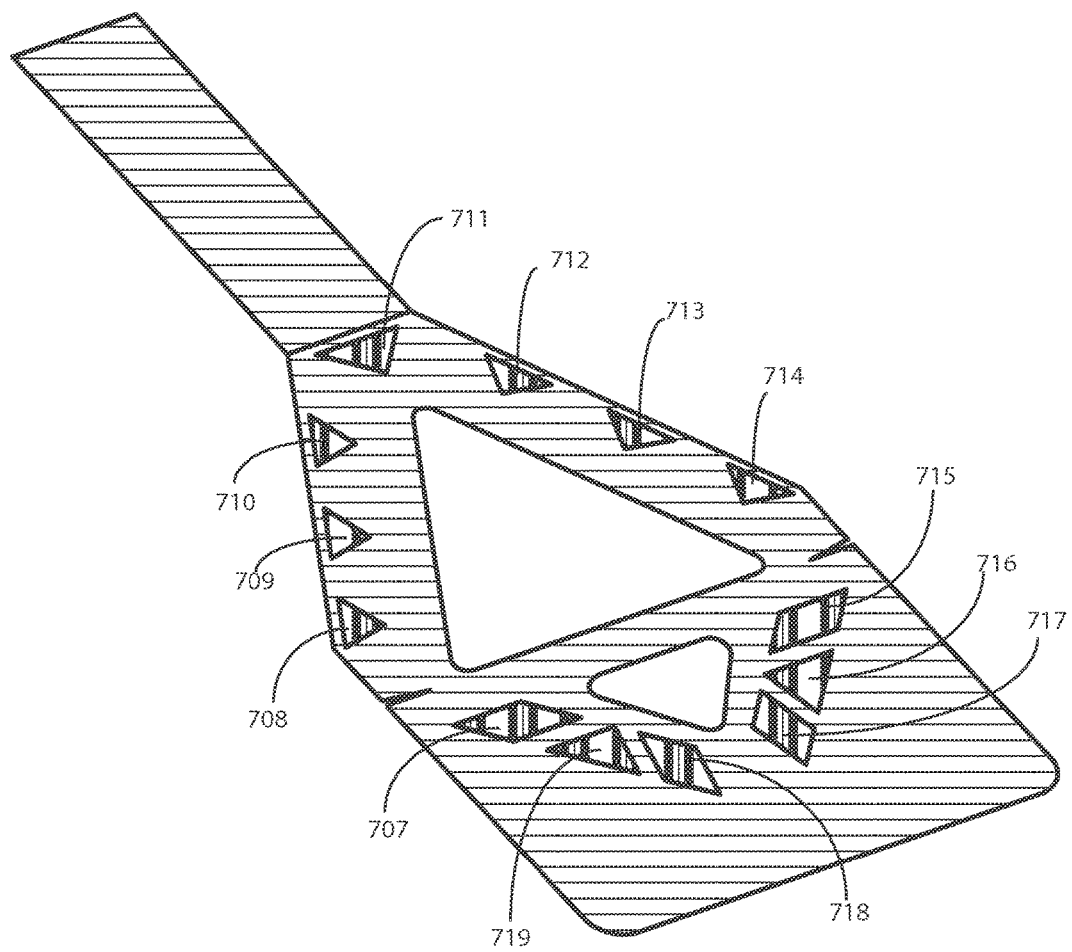
FIG. 7 illustrates another step in a method of manufacturing an explanatory dressing assembly configured in accordance with one or more embodiments of the invention.

Turning to FIG. 7, a second selective printing process has deposited a higher adhesion coefficient in the voids (407, 408,409,410,411,412,413,414,415,416,417,418,419) to form adhesive islands 707,708,709,710,711,712,713,714, 715,716,717,718,719.

Figure 8:
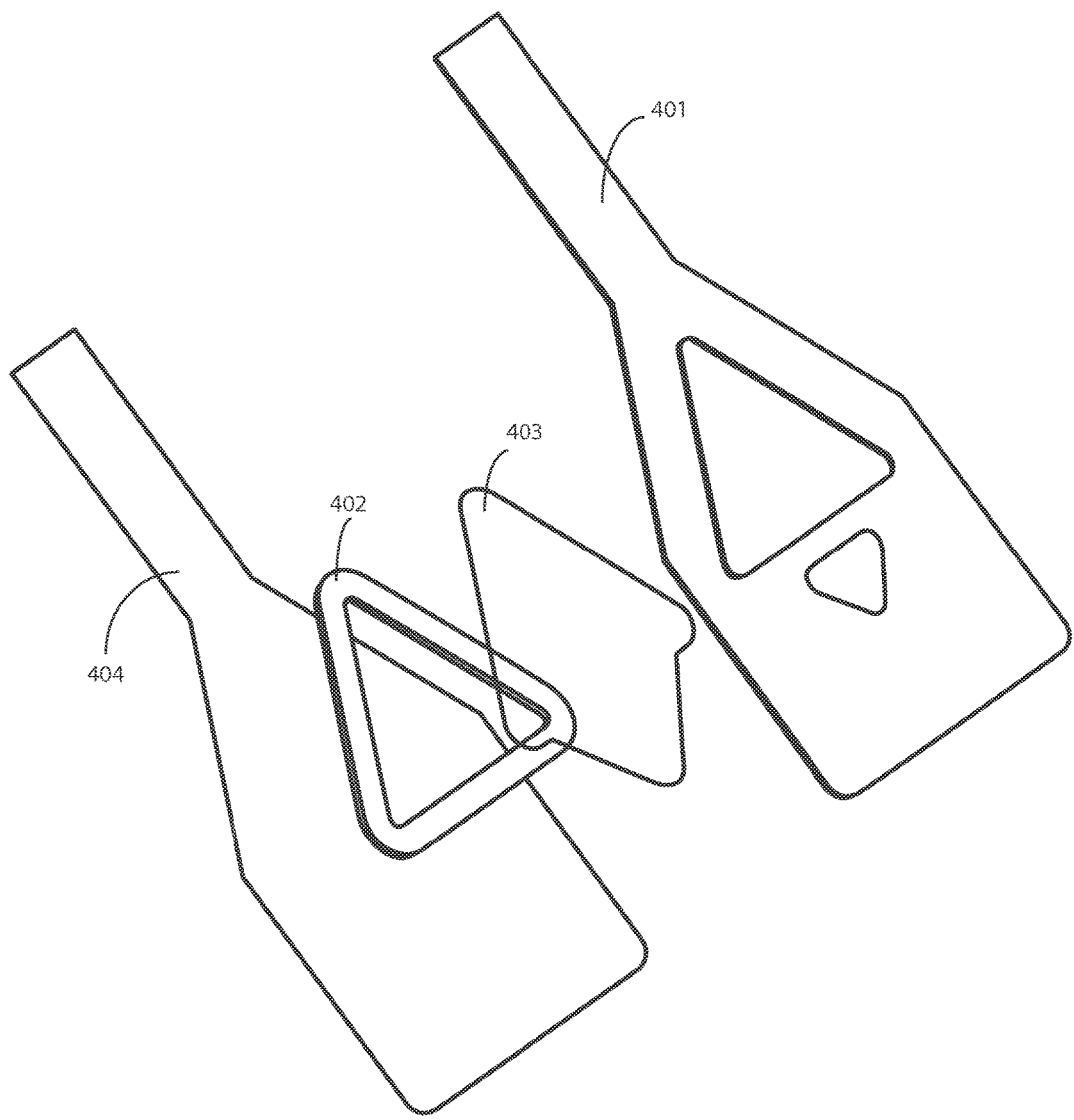
FIG. 8 illustrates another step in a method of manufacturing an explanatory dressing assembly configured in accordance with one or more embodiments of the invention.

Turning to FIG. 8, the backing layer 403 and adsorptive surround 402 are coupled to the cover layer 401. In one embodiment, these elements are adhesively coupled to the backing layer 403. However, other coupling mechanisms can be used. For example, the backing layer 403 can be thermally coupled to the cover layer 401, while the absorptive surround is adhesively coupled to the backing layer 403 and/or the cover layer 401. Once the constituent elements are coupled together, regardless of process, the wax release backing paper 404 can be applied to the adhesive layer (620) and adhesive islands (707,708,709,710,711,712,713,714, 715,716,717,718,719) to prevent them from sticking to anything prior to use.

Figure 9:
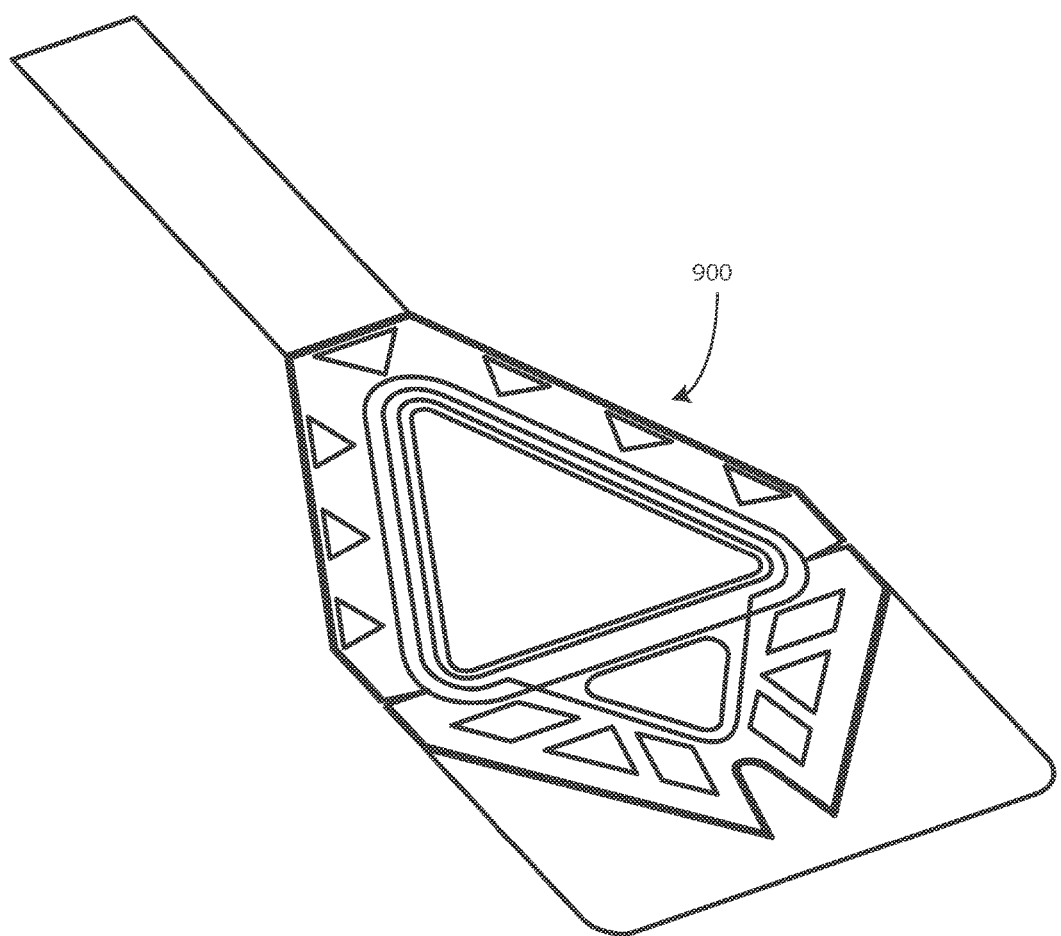
FIG. 9 illustrates another step in a method of manufacturing an explanatory dressing assembly configured in accordance with one or more embodiments of the invention.

In one embodiment, the backing layer 403 has adhesive applied to its bottom side. In another embodiment, the backing layer 403 includes no adhesive. Where the backing layer 403 is to include adhesive, it can be coupled to the cover layer 401 at an earlier stage. For instance, the backing layer 403 can be attached to the cover layer 401 prior to the step occurring at FIG. 6. Accordingly, when the adhesive layer (620) is applied, it can be applied to the backing layer as well. The completed dressing assembly 900 is shown in FIG. 9 in a bottom perspective view.

Rather than manufacturing dressings individually, the advantageous shape associated with embodiments of the invention lend themselves to palletized manufacture. This benefit of the overall shape is in addition to the adhesion benefits described above. One such pallet 1000 is shown in FIG. 10.

Figure 10:
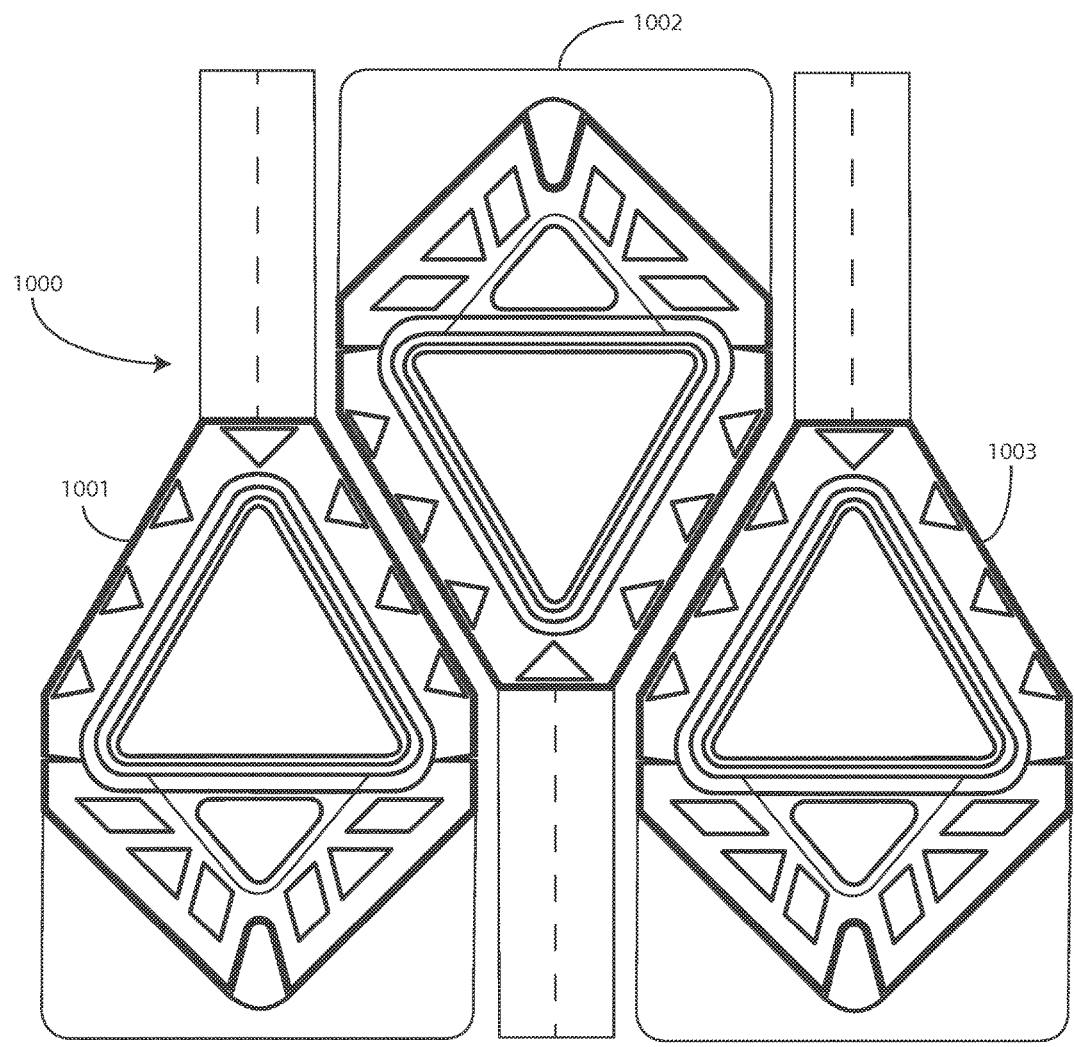
FIG. 10 illustrates one explanatory panel of dressing assemblies configured in accordance with one or more embodiments of the invention.

Turning now to FIG. 10, the pallet 1000 includes multiple dressing assemblies 1001,1002,1003, with every other dressing assembly being rotated 180 degrees out of phase with reference to its neighbor. Thus, dressing assembly 1002 is 180 degrees out of phase relative to dressing assembly 1001 and dressing assembly 1003. The dressing assemblies 1001,1002,1003 can be manufactured in a single sheet in this fashion, with each being separated by a cutting process post manufacture. This can be done with far less waste than is normally associated with prior art dressing designs. Note that while three dressing assemblies 1001,1002,1003 are shown in FIG. 10, the pallet 1000 can include more, either extending horizontally or vertically by adding more dressing assemblies or rows of dressing assemblies, respectively.

Figure 11:
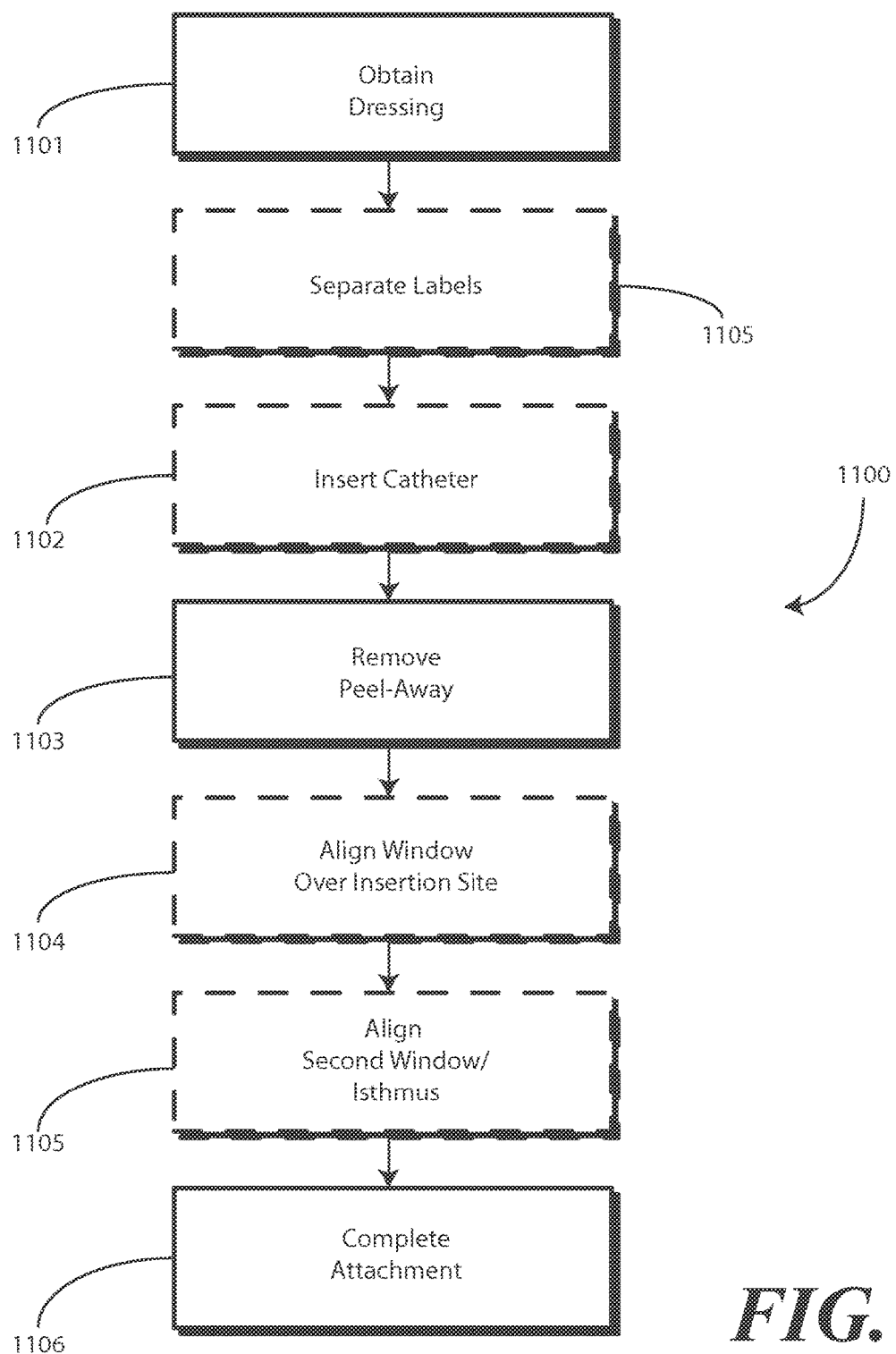
FIG. 11 illustrates one explanatory method of using a dressing configured in accordance with one or more embodiments of the invention.

Turning now to FIG. 11, illustrated therein is a method of using one or more of the dressing assemblies described above. Beginning with step 1101, a user or medical practitioner first acquires a dressing assembly configured in accordance with one or more embodiments of the invention. In one embodiment, such a dressing assembly comprises a top layer defining a window, a backing layer coupled to the top layer and spanning the window, and a plurality of adhesive islands disposed about a perimeter of the top layer. The adhesive islands can have a first adhesion coefficient associated therewith. An adhesive layer can be disposed about the adhesive islands such that the adhesive layer completely surrounds each of the adhesive islands. The adhesive layer can have a second adhesion coefficient associated therewith. The second adhesion coefficient can be less than the first adhesion coefficient. In another embodiment, the dressing assembly comprises a cover layer and a plurality of force concentration elements disposed about a perimeter of the cover layer. Each force concentration element can be configured to collect and distribute shearing forces applied to the dressing so as to retain the dressing—and optionally a catheter—to a patient.

Where the method includes the insertion of a catheter, the catheter can be inserted at optional step 1102. At step 1103, the user or medical practitioner removes the releasable, wax, peel-away layer to expose the adhesive disposed along the cover or top layer of the dressing. Note that this step 1103 can occur prior to, or after, step 1102.

Where the method includes the insertion of a catheter and the dressing is a window dressing, optional step 1104 can include placing a window of the window dressing atop the insertion site. Similarly, where the dressing is a dual window dressing, optional step 1105 can include placing a second window of the dual window dressing atop a coupler of the catheter such that at least a portion of the coupler is disposed beneath the dressing under an isthmus disposed between the window and the second window. Application of the dressing to the patient can then be completed at step 1106.

Where the dressing includes adhesively backed labels, these labels can be separated from the dressing at optional step 1105. They can be used at this step as described above, or alternatively discarded. In one embodiment, step 1105 occurs before the application of the dressing, although it can come after as well.

Figure 12:
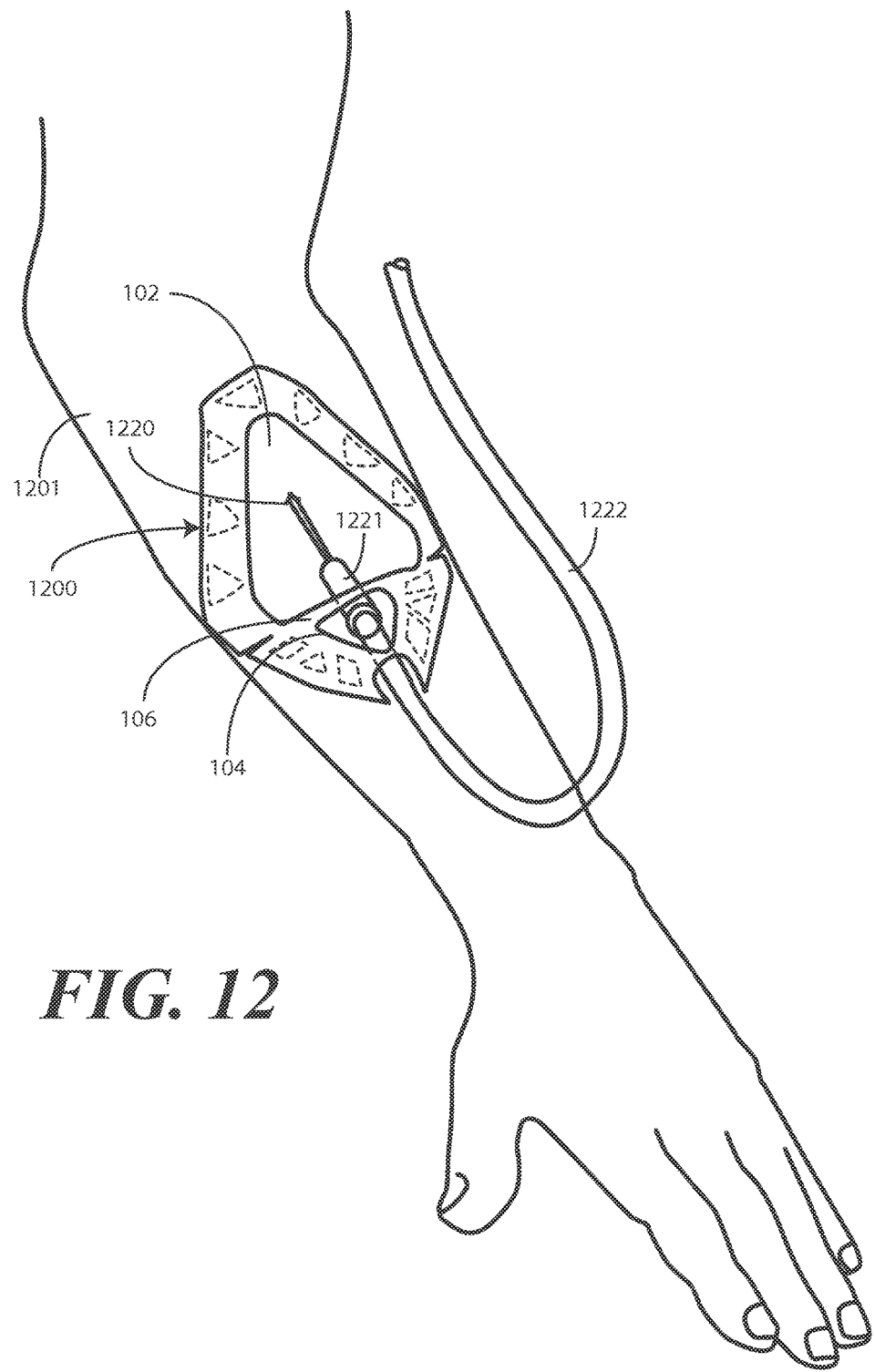
FIG. 12 illustrates one explanatory dressing configured in accordance with the invention in use on a patient undergoing a catheterization process.

FIG. 12 shows one embodiment of a dressing 1200 having been applied to a patient 1201 in accordance with the method (1100) of FIG. 11. As shown in FIG. 12, a first window 102 of the dressing 1200 is disposed over an insertion site 1220. A second window 104 is disposed over a base 1221 of a catheter assembly such that an isthmus 106 of the dressing passes atop at least a portion of the base 1221. Tubing 1222 of the catheter passes from beneath the dressing 1200 at a concave inlet 128. In this configuration, both the dressing 1200 and catheter are securely retained to the patient.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A window dressing, comprising:
   a top layer defining a window;
   a backing layer coupled to the top layer and spanning the window;
   a plurality of adhesive islands disposed about a perimeter of the top layer, each adhesive islands having a first adhesion coefficient associated therewith; and
   an adhesive layer disposed about the plurality of adhesive islands, the adhesive layer having a second adhesion coefficient associated therewith that is less than the first adhesion coefficient.

2. The window dressing of claim 1, wherein one or more of the adhesive islands are configured to be visibly distinct from the adhesive layer.

3. The window dressing of claim 2, wherein the one or more adhesive islands and the adhesive layer have different colors.

4. The window dressing of claim 1, wherein at least some of the plurality of adhesive islands have one of triangular perimeters or rectangular perimeters.

5. The window dressing of claim 4, wherein at least some others of the plurality of adhesive islands have another of the triangular perimeters or the rectangular perimeters.

6. The window dressing of claim 1, wherein the plurality of adhesive islands comprises at least twelve adhesive islands.

7. The window dressing of claim 1, wherein the window is generally triangular.

8. The window dressing of claim 7, wherein the top layer defines stress relief elements that are substantially aligned with one side of the window.

9. The window dressing of claim 1, wherein the top layer comprises a plurality of layers.

10. The window dressing of claim 9, wherein one of the plurality of layers is colored.

11. The window dressing of claim 1, wherein the plurality of adhesive islands is deposited on a bottom of the top layer by a selective printing process.

12. The window dressing of claim 1, wherein the plurality of adhesive islands are disposed on a patient side of the top layer.

13. The window dressing of claim 1, wherein a portion of the window dressing is substantially trapezoidal in shape.

14. The window dressing of claim 13, wherein another portion of the window dressing is substantially inverted-peak triangular in shape.

15. The window dressing of claim 1, further comprising two adhesively backed label strips coupled to the window dressing at one of a score line or perforation and extending distally from the window dressing.

16. The window dressing of claim 1, wherein the plurality of adhesive islands and the adhesive layer are disposed on a common side of the top layer.

17. The window dressing of claim 16, wherein the common side comprises a bottom side of the top layer.

18. The window dressing of claim 1, wherein the adhesive layer surrounds each adhesive island of the plurality of adhesive islands on one side of the top layer.

\* \* \* \* \*